United States Patent [19]

Hutt et al.

[11] Patent Number: 5,380,741
[45] Date of Patent: Jan. 10, 1995

[54] FUNGICIDAL TRIAZOLE AND IMIDAZOLE DERIVATIVES

[75] Inventors: Jean Hutt; Marie-Pascale Latorse, both of Lyon; Christine Veyrat, St Cyr Au Mont-D'Or, all of France

[73] Assignee: Rhone-Poulenc Agrochimie, Lyon Cedex, France

[21] Appl. No.: 44,048

[22] Filed: Apr. 8, 1993

[30] Foreign Application Priority Data

Apr. 8, 1992 [FR] France ................. 92 04524

[51] Int. Cl.$^6$ ................. A01N 43/653; C07D 249/08
[52] U.S. Cl. ................. 514/383; 548/267.2; 548/267.4; 548/267.8; 548/268.6
[58] Field of Search ........ 514/383; 548/267.2, 548/267.4, 267.8, 268.6

[56] References Cited

U.S. PATENT DOCUMENTS

| | | | |
|---|---|---|---|
| 3,563,741 | 2/1971 | Delzenne et al. | 96/35.1 |
| 4,532,341 | 7/1985 | Holmwood et al. | 549/559 |
| 4,871,390 | 10/1989 | Holmwood et al. | 71/92 |
| 4,897,107 | 1/1990 | Holmwood et al. | 71/92 |
| 4,904,298 | 2/1990 | Holmwood et al. | 71/92 |
| 4,952,232 | 8/1990 | Cuomo et al. | 71/92 |
| 4,965,280 | 10/1990 | Cuomo et al. | 514/383 |
| 4,965,281 | 10/1990 | Cuomo et al. | 514/399 |
| 4,980,367 | 12/1990 | Cuomo et al. | 548/267.8 |
| 5,017,595 | 5/1991 | Seele et al. | 514/383 |
| 5,057,531 | 10/1991 | Seele et al. | 514/383 |
| 5,057,532 | 10/1991 | Seele et al. | 514/383 |
| 5,179,114 | 1/1993 | Seele et al. | 514/383 |
| 5,256,683 | 10/1993 | Hutt et al. | 514/383 |

FOREIGN PATENT DOCUMENTS

| | | |
|---|---|---|
| 2054342 | 4/1992 | Canada . |
| 0212605 | 3/1987 | European Pat. Off. . |
| 0341954 | 11/1989 | European Pat. Off. . |
| 0345639 | 12/1989 | European Pat. Off. . |
| 0378953 | 7/1990 | European Pat. Off. . |
| 0433780 | 6/1991 | European Pat. Off. . |
| 0461502 | 12/1991 | European Pat. Off. . |
| 0483616 | 5/1992 | European Pat. Off. . |
| 0486409 | 5/1992 | European Pat. Off. . |
| 1179866 | 2/1970 | United Kingdom . |
| 89/05581 | 6/1989 | WIPO . |

Primary Examiner—Patricia L. Morris
Attorney, Agent, or Firm—Burns, Doane, Swecker & Mathis

[57] ABSTRACT

The invention relates to new compounds containing a triazole or imidazole group having plant protection use of general formula:

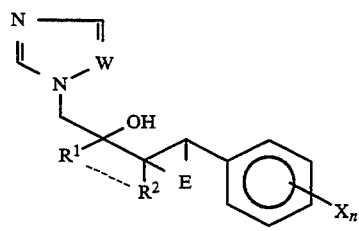

in which:
W is N or CH;
E is $CH_2$ or O;
X is a halogen or an alkyl radical;
n is an integer from 0 to 5;
$R^1$ is an alkyl, a cycloalkyl or an aryl;
$R^2$ is an alkyl or a perfluoroalkyl.

The invention also relates to the preparation of these compounds and to their use as broad-spectrum fungicides.

23 Claims, No Drawings

FUNGICIDAL TRIAZOLE AND IMIDAZOLE DERIVATIVES

The present invention relates to new compounds containing a triazole or imidazole group having plant protection use. It also relates to the processes for the preparation of these compounds and to the compounds which can optionally be used as intermediates in the preparation processes. It finally relates to the fungicidal use of these compounds, to the fungicidal compositions based on these compounds and to the processes for controlling fungal crop diseases using these compounds. It also relates to a propagation material for crop plants which has been subjected to a protection treatment using a product of the invention.

One of the aims of the present invention is to provide compounds exhibiting an improved activity in the treatment of fungal diseases.

Another aim is to provide compounds exhibiting a use spectrum which is also improved in the field of fungal diseases.

Many products containing triazole groups, especially fungicides, are already known. In particular, triazole fungicides containing a tetrahydrofuran ring are known from the Patent Applications EP 151,084, EP 246,982, EP 121,979 and EP 89,100. Triazole fungicides containing a cyclopentane ring are known from the Patent Applications EP 272,895, EP 267,778, EP 378,953, DE 3,630,840 and BE 867,245. Triazole fungicides containing a cycloalkane group are known from the Patent Application EP 324,646 and U.S. Pat. No. 4,684,396.

Other fungicidal triazole or imidazole compounds are described in the patent literature. Certain triazoles or imidazoles containing a cyclopropyl group are known from the Patent Applications BE 886,128, EP 40,345, EP 47,594, EP 52,424, EP 143,384, EP 180,136, EP 180,838, EP 212,605 and DE 3,909,862. Certain triazoles or imidazoles containing an oxirane group are described in the Patent Applications EP 251,086 and DE 3,819,053.

Thus, taking into account the state of the art, one aim of the present invention is to provide other broad-spectrum fungicidal triazole or imidazole compounds which are useful especially in the treatment of stalk diseases, such as cereal eyespot, or leaf diseases, such as powdery mildew or diseases caused by Septoria, Piricularia, Fusarium, Rhynchosporium or Rhizoctonia species, or diseases caused by pathogenic fungi such as Botrytis, Phoma or Ascochyta, in crops as diverse as cereals, vines, rice, maize and soya, for example.

It has now been found that the abovementioned aims could be achieved by virtue of the compounds according to the invention, which are new derivatives containing a triazole or imidazole group and an oxirane or cyclopropyl group, optionally substituted. These compounds have the general formula VII:

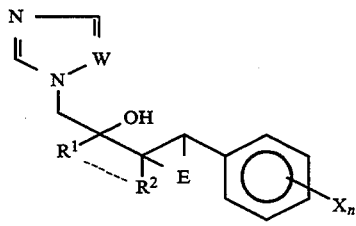

(VII)

in which:

$R^1$ represents a linear or branched alkyl radical containing 1 to 4 carbon atoms; a cycloalkyl radical containing 3 to 6 carbon atoms; an alkylidene, hydroxyalkyl or carboxyalkyl radical containing 1 to 4 carbon atoms, these radicals optionally being substituted by one or a number of halogen atoms; an aryl radical, chosen from the group comprising phenyl or naphthyl, optionally substituted by one or a number of groups chosen from halogen, nitro, cyano, amino, alkyl or alkoxy containing 1 to 4 carbon atoms optionally substituted by one or a number of halogen atoms, or alkylamino, the alkyl part having from 1 to 4 carbon atoms optionally substituted by one or a number of halogen atoms; or an aralkyl radical, the linear or branched alkyl part of which has from 1 to 4 carbon atoms and the aryl part of which is defined as above;

$R^2$ represents a linear or branched alkyl or perhaloalkyl radical having 1 to 4 carbon atoms, or a halogen atom, preferably chlorine or fluorine, when E is other than an oxygen atom;

$R^1$ and $R^2$, together, can form a —(CH$_2$)$_3$—, —(CH$_2$)$_4$— or —(CH$_2$)$_5$— radical, thus leading to a ring containing 5, 6 or 7 carbon atoms, in which ring each hydrogen can optionally be substituted by a radical chosen from the group comprising the halogen atoms or the linear or branched alkyl radicals containing 1 to 4 carbon atoms optionally substituted by one or a number of halogen atoms;

W is a CH radical or a nitrogen atom;

E represents an oxygen atom or a CH$_2$ radical;

X represents an F, Cl or Br halogen atom; a linear or branched alkyl radical containing 1 to 4 carbon atoms optionally substituted by one or a number of halogen atoms; an alkylamino radical, the alkyl part having from 1 to 4 carbon atoms optionally substituted by one or a number of halogen atoms; an alkoxy radical containing 1 to 4 carbon atoms optionally substituted by one or a number of halogen atoms; a phenoxy or benzyloxy radical which is optionally substituted by one or a number or halogens; nitro; or cyano;

n is an integer equal to 1, 2, 3, 4 or 5 with, when this integer is greater than or equal to 2, the possibility that the groups X are not identical.

The invention also relates to the salt forms of the above defined compounds. The salt forms are the forms which are acceptable in agriculture, among which there may be mentioned the hydrochlorides, sulphates, oxalates, nitrates or alkyl- or arylsulphonates, as well as the addition complexes of these compounds with metal salts, and especially iron, chromium, copper, manganese, zinc, cobalt, tin, magnesium and aluminium salts.

The compounds of the invention and the compounds which can optionally be used as intermediates in the processes of preparation, and which will be defined when describing these processes, can exist in one or a number of isomeric forms depending on the number of asymmetric centres in the molecule. The invention thus also relates to all the optical isomers as well as to their racemic mixtures and to the corresponding diastereoisomers, whether separate or in combination. The separation of the optical isomers and/or of the diastereoisomers can be carried out according to methods known per se.

Among the compounds of the invention, those in which W is a nitrogen atom, i.e. the triazole compounds, will be preferred for the purposes of fungicidal applications.

In a still more advantageous way, triazole compounds having an oxirane or cyclopropane group will be chosen.

Finally, the compounds in which X represents a halogen, preferably chlorine, $R^1$ is a linear or branched propyl or butyl group, and $R^2$ is a methyl or ethyl radical, or in which $R^1$ and $R^2$ together form a ring containing 5 or 6 carbon atoms, constitute a group of preferred compounds among the compounds of the invention containing triazole groups and an oxirane or cyclopropane group.

The invention also relates to the preventative or curative use of the above defined compounds as fungicides and to the fungicidal compositions. The compounds of the invention can be used in leaf treatment, in soil treatment or, in view of the absence of phytotoxicity, in seed treatment.

The invention also relates to a process for the treatment of crops affected by or capable of being affected by fungal diseases, characterised in that an effective dose of a compound of the invention is applied to the leaves.

The compounds are advantageously applied in doses of 0.002 to 5 kg/ha, and more specifically of 0.005 to 1 kg/ha.

The invention additionally relates to a propagation material for crop plants which has been subjected to a protection treatment with a compound of the invention.

Propagation material denotes all the generative parts of the plant which can be used for the propagation of the latter. There may be mentioned, for example, the seeds (used in the strictest sense of the term), roots, fruits, tubers, bulbs, rhizomes, stem parts, seedlings, shoots and other plant parts. There should also be mentioned the germinated plants and the young plants which have to be transplanted after germination or after emerging from the ground. These young plants can be protected before transplantation by a total or partial treatment by immersion.

In general, the compounds will be applied at a concentration of 0.1 to 500 g per quintal of seeds. The seeds will then be subjected to treatment with the compounds according to the invention by coating or pelleting. Patents US 3,989,501 and FR 2,588,442 describe such forms of application.

Another subject of the present invention is processes for the preparation of the compounds according to the invention and the compounds which can optionally be used as intermediates in the preparation processes.

A first set of processes, given in Scheme A below, involves the intermediate compounds of formulae II, III, IV, V, VI, VIII and IX, in which the substituents W, E, $R^1$, $R^2$, X and n have the same meaning as in the general formula VII above.

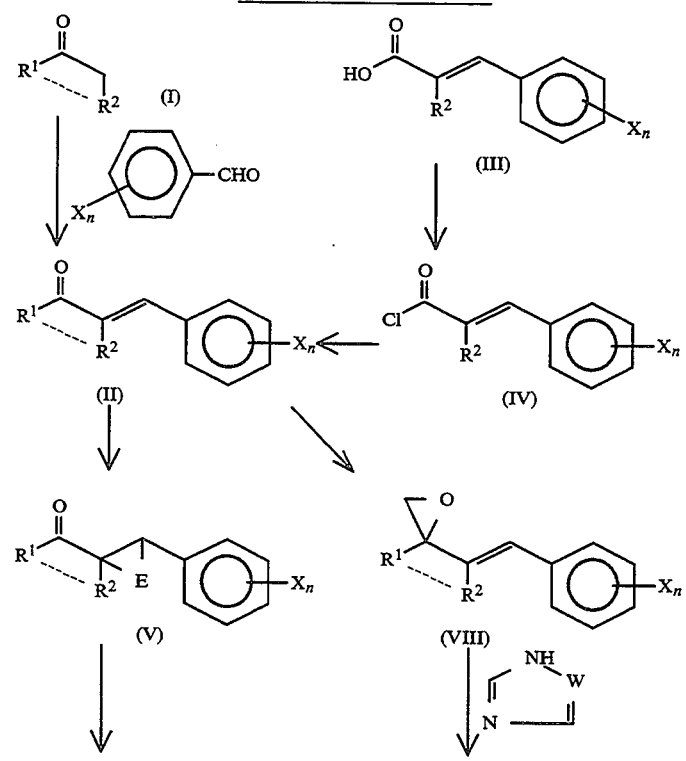

REACTION SCHEME A:

REACTION SCHEME A:

-continued

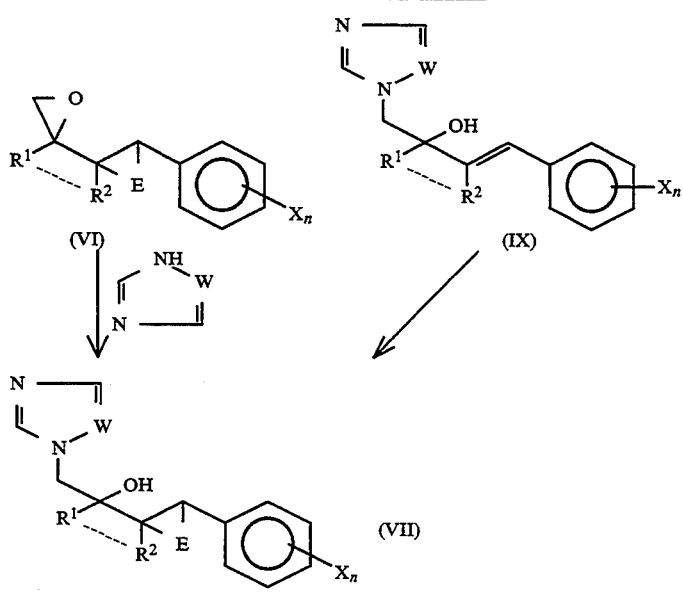

The process consists in condensing a ketone of general formula (I)

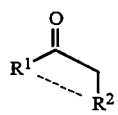 (I)

with an aldehyde of formula:

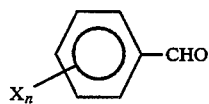

in the presence of a base, such as alkali metal or alkaline-earth metal hydroxides, alkali metal alkoxides, sodium hydride or lithium amides, or of an acid, such as sulphuric acid, acetic acid, hydrochloric acid, hydrobromic acid, p-toluenesulphonic acid or methanesulphonic acid, in a solvent such as a $C_1$ to $C_5$ alcohol or an ether or an aromatic hydrocarbon, by means of the well known aldol condensation/dehydration reaction so as to obtain the compound of formula (II)

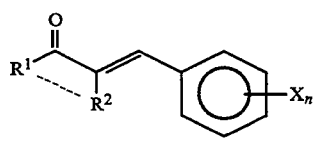 (II)

Generally, the ketones of formula (II), in which $R^1$ and $R^2$ together form a ring, can be obtained according to the methods described in the application EP 378,953. They can, in particular, be obtained by reacting an aldehyde of formula:

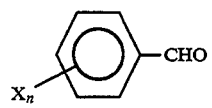

with an anhydride of formula $(R^2CH_2CO)_2O$ and the sodium or potassium salt of the corresponding carboxylic acid $R^2CH_2CO_2H$ according to the Perkin reaction described in Org. React., 1, 251 (1942) in order to obtain a cinnamic acid derivative of formula (III)

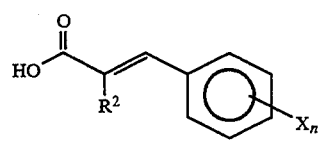 (III)

The compound (III) is converted to the acid chloride (IV)

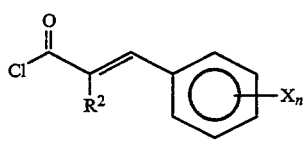 (IV)

using thionyl chloride, phosphorus trichloride, phosphorus pentachloride, oxalyl chloride or the triphenylphosphine/carbon tetrachloride complex.

The ketone (II) is then obtained by:
coupling the acid chloride (IV) with an organomagnesium compound $R^1MgCl$ or an organozinc compound $R^1_2Zn$ in a solvent such as ether or tetrahydrofuran with a temperature range of $-78°$ to $+25°$ C. in the absence or in the presence of copper and of cuprous chloride according to the method described in the literature (J. E. Dubois, M. Boussu, Tetrahedron Lett., 1970, 2523);

coupling the acid chloride (IV) with the lithium, sodium or potassium enolate of butyrolactone in THF, followed by decarboxylation in the presence of LiCl, LiBr, NaCl or NaBr in a solvent such as dimethyl sulphoxide, N,N-dimethylformamide or N-methyl-2-pyrrolidinone at a temperature between room temperature and the reflux temperature of the solvent according to the method described in the literature (S. Takei, Y. Kawano, *Tetrahedron Lett.*, 1975, 4389);

coupling the acid chloride (IV) with the lithiated dianion of the carboxylic acid $R^1COOH$ (provided that $R^1$ has at least one hydrogen atom) in a solvent such as tetrahydrofuran or ether followed by a decarboxylating acid treatment according to the method described in the literature (P. E. Pfeffer, L. S. Silbert, J. M. Chirinko, *J. Org. Chem.*, 1972, 37, 451);

coupling the amide, obtained in a way known per se from the acid chloride by reaction with a, preferably secondary, amine, with an organomagnesium or organolithium compound, as described by S. M. Weinreb et al., *Tetrahedron Letters*, 1981, vol 22, pp 3815-3818.

The compound of formula (II) is reacted with a sulphoxonium ylide, of formula $(CH_3)_2S(O)=CH_2$, obtained by reacting a base, such as an alkali metal alkoxide, NaH or alkali metal hydroxides, with a halide, for example trimethylsulphoxonium iodide $((CH_3)_3SO^+I^-)$, in a solvent such as dimethyl sulphoxide, N,N-dimethylformamide, N-methyl-2-pyrrolidinone or acetonitrile, or a mixture of these solvents with tert-butyl alcohol or tert-amyl alcohol in a 50:50 to 90:10 ratio at a temperature of between 20° and 100° C. to obtain the compound of formula (V). The compound of formula (II) can also be reacted with hydrogen peroxide or with tert-butyl hydroperoxide in the presence of a base such as an alkali metal hydroxide in a water/$C_1$-$C_5$ alcohol mixture in a temperature range of between 0° C. and the reflux temperature of the solvent to obtain compound of formula (V)

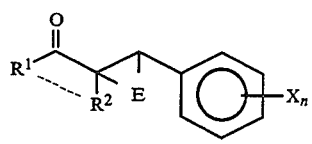

(V)

The said compound (V) is reacted with a sulphonium ylide of formula $(CH_3)_2S=CH_2$, obtained by reacting a base such as alkali metal hydroxides, NaH or alkali metal alkoxides with $((CH_3)_3S^+X^-)$ (X=Cl, Br, I, or $CH_3SO_4$), in a solvent such as dimethyl sulphoxide, N,N-dimethylformamide, N-methyl-2-pyrrolidinone, acetonitrile or a dichloromethane/water or toluene/water mixture at a temperature of between −10° C. and +50° C. to obtain an oxirane of formula (VI)

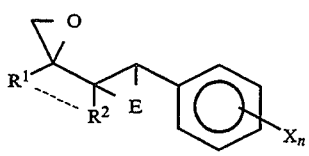

(VI)

This oxirane can also be obtained by reacting a halomethyllithium compound with a compound of formula (V) as described in *Bull. Soc. Chim. de France*, 1986, vol 3, pp 470–477.

The oxirane (VI) is reacted with a nitrogenous heterocycle of general formula

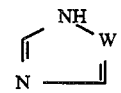

in the presence of bases such as NaH, alkali metal hydroxides, alkali metal alkoxides or sodium or potassium carbonate in a solvent such as N-methyl-2pyrrolidinone, N,N-dimethylformamide, dimethyl sulphoxide, $C_1$-$C_5$ alcohols or nitriles in a temperature range of between +25° C. and the reflux temperature of the solvent to obtain a compound of formula (VII):

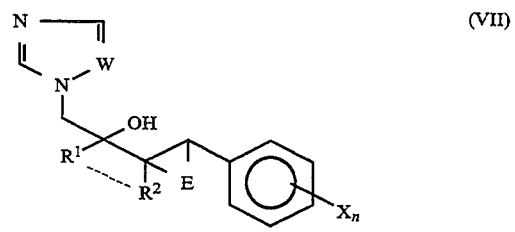

(VII)

The compounds of formula (VII) can also be obtained from the compound (II) as described in the Patent EP 378,953-A by reaction with a sulphonium ylide, of formula $(CH_3)_2S=CH_2$, obtained by reacting a base such as alkali metal hydroxides, NaH or alkali metal alkoxides with $((CH_3)_3S^+X^-)$ (X=Cl, Br, I, or $CH_3SO_4$), in a solvent such as dimethyl sulphoxide, N,N-dimethylformamide, N-methyl-2-pyrrolidinone, acetonitrile or a dichloromethane/water or toluene/water mixture at a temperature of between −10° C. and +50° C. to obtain an oxirane of formula (VIII)

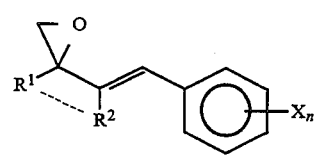

(VIII)

The said oxirane is reacted with a nitrogenous heterocycle of general formula

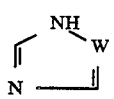

in the presence of bases such as NaH, alkali metal hydroxides, alkali metal alkoxides or sodium or potassium carbonate in a solvent such as N-methyl-2-pyrrolidinone, N,N-dimethylformamide, dimethyl sulphoxide, $C_1$-$C_5$ alcohols or nitriles in a temperature range of between +25° C. and the reflux temperature of the solvent to obtain a compound of formula (IX)

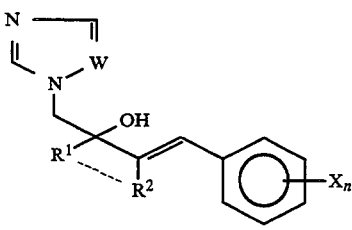
(IX)

In the case where E is CH$_2$, the compound of formula (IX) is subjected to a cyclopropanation reaction of the Simmons-Smith type (cf. *Organic Reactions*, 1973, vol 20, p 1-131) with a dihalomethane, preferably diiodo or dibromo. A variation consists in carrying out the reaction under ultrasound as described in *Tetrahedron Letters*, 1982, vol 23, pp 2729-2732 or according to British Application 2,191,774.

In the case where E is an oxygen atom, the compound of formula (IX) is subjected to an oxidation with meta-chloroperbenzoic acid or tert-butyl hydroperoxide in a solvent such as halogenated solvents or hydrocarbons to obtain the compound according to the invention of formula (VII).

A second set of processes, as given in Scheme B below, involves the intermediate compounds of formulae X, XI, XII and XIII, in which the substituents w, E, $R^1$, $R^2$, X and n have the same meaning as in the general formula VII above and:

$R^3$ represents a halogen atom, preferably chlorine or bromine, or a group Y-$R^4$, in which Y represents an oxygen, sulphur or nitrogen atom and $R^4$ represents a hydrogen atom, a linear or branched alkyl radical containing 1 to 4 carbon atoms, a cycloalkyl radical containing 3 to 6 carbon atoms, a phenyl or naphthyl radical, optionally substituted by 1 to 5 substituents chosen from the group comprising a halogen atom, amino or alkyl or alkoxy containing 1 to 4 carbon atoms, or also a phenylalkyl or naphthylalkyl radical, the alkyl part of which comprises 1 to 4 carbon atoms. In the case where Y is a nitrogen atom, it carries, in addition to $R^4$, a second substituent which is identical to or different from $R^4$ and which can have the same meanings.

$R'^3$ represents a halogen atom (identical to $R^3$, when $R^3$ is a halogen atom), or a sulphonium or sulphoxonium salt, preferably $C_1$-$C_4$ alkylsulphonium or $C_1$-$C_4$ alkylsulphoxonium, when Y is a sulphur atom, an ammonium salt (preferably $C_1$-$C_4$ alkylammonium), when Y is a nitrogen atom or an alkane(preferably methane)sulphonate, benzene(preferably tolyl)sulphonate or naphthalenesulphonate group, or a haloalkylcarbonyloxy (preferably trifluoromethylcarbonyloxy) group, when Y is an oxygen atom.

The compounds of formula X, in which $R^3$ is a halogen atom, can be prepared by reacting a compound of formula II and a halomethyllithium compound according to the method described in *Bull. Soc. Chim. Fr.*, 1986, pp 470-477).

The compounds of formula X, in which $R^3$ is the group $YR^4$, can be prepared by reacting a compound of formula II and a compound HY$R^4$, according to the method described by *Advanced Organic Chemistry*, McGraw Hill Inc., J. March.

The compounds of formula X, in which $R^3$ is the group $YR^4$ in which Y is a sulphur atom, can be prepared by reacting a compound of formula II and an alkyl(or aryl)thiomethyllithium compound according to the method described in *J. Org. Chem.*, 1985, vol 95, pp 3429-3431.

The compounds of formula X, in which $R^3$ is the hydroxyl group, can be prepared by reacting a compound of formula II with paraformaldehyde according to the method described in *Tetrahedron Letters*, 1992, vol 48, pp 2069-2080.

The compounds of formula XI can be prepared by reacting, according to a cyclopropanation reaction of the Simmons-Smith type (cf *Organic Reactions*, 1973, vol 20, p 1-131), with a dihalomethane, preferably diiodo or dibromo. A variation consists in carrying out the reaction under ultrasound as described in *Tetrahedron Letters*, 1982, vol 23, pp 2729-2732 or according to British Application 2,191,774. In the case where $R^3$ is a group $SR^4$, in which $R^4$ is a linear or branched alkyl radical containing 1 to 4 carbon atoms or a cycloalkyl radical containing 3 to 6 carbon atoms, compounds of formula XII, in which $R'^3$ represents a methylsulphonium halide (preferably an iodide), are obtained directly from the compounds of formula X.

The compounds of formula XII, in which $R'^3$ is an alkanesulphonate, benzenesulphonate or naphthalenesulphonate group, or haloalkylcarbonyloxy group, can be obtained from a compound of formula XI, in which $R^3$ is the hydroxyl group, according to the method described by *Advanced Organic Chemistry*, McGraw Hill Inc., J. March.

The compounds of formula XI can be obtained directly from a compound of formula X, in which $R^3$ is the hydroxyl group, or from a compound of formula XI, in which $R^3$ is an alkoxy or aryloxy group, according to the known methods, in particular by reacting with trimethylsilyl iodide as described in *Silicon Reagents for Organic Synthesis*, W. P. Weber, 1983, Springer Verlag.

The compounds of formula XIII can be obtained from the compounds of formula XII by reacting with a base such as an alkali metal hydroxide, sodium hydride or an alkali metal alkoxide in a solvent such as dimethyl sulphoxide, N,N-dimethylformamide, N-methyl-2-pyrrolidinone or acetonitrile at a temperature of from $-10°$ C. to $+60°$ C.

REACTION SCHEME B
(in relative configuration)

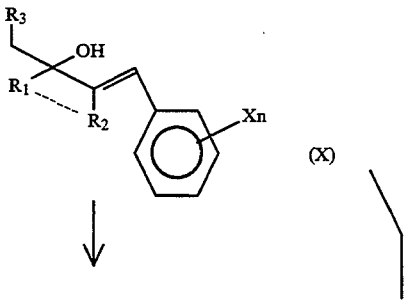
(X)

-continued
REACTION SCHEME B
(in relative configuration)

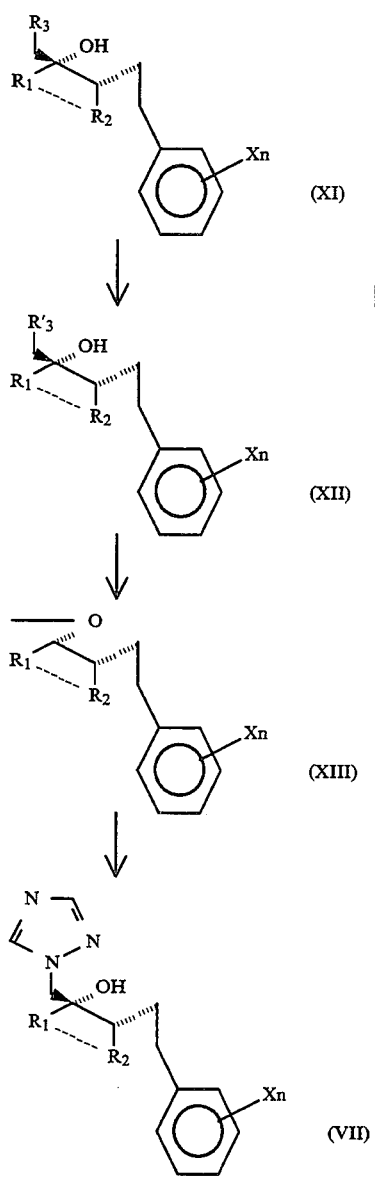

The compounds of formula VII, in which E is the methylene group, can be obtained from the compounds of formula XIII according to the same method as that described above from the compounds of formula VI.

The examples below are given by way of illustration of the compounds according to the invention, of the processes for their preparation and of their antifungal properties.

Example 1

Preparation of
1-(4-chlorophenyl)-2,4-dimethyl-1-penten-3-one

Hydrogen chloride is sparged into a mixture of 100 ml of 2-methyl-3-pentanone, 113 g of 4-chlorobenzaldehyde and 400 ml of ethanol until saturated. The temperature of the solution is maintained at 60° C. for 8 h. The mixture is then poured into 1 l of water and extracted with 500 ml of diisopropyl ether. The organic phase is washed with 250 ml of 10% sodium hydroxide solution, then with 250 ml of saturated sodium chloride solution and dried over sodium sulphate. After evaporation, 167 g of a brown liquid are obtained.
Y=93%.

Example 2

Preparation of
1-(4-chlorophenyl)-2-methyl-2-(2-methylpropionyl)cyclopropane 185 ml of tert-amyl alcohol are added to a suspension of 61.3 g of sodium hydride in 200 ml of NMP heated to 50° C. so as to have a steady evolution of hydrogen. The solution obtained is cooled to 25° C. and 176 g of solid trimethylsulphoxonium iodide are added, followed by a solution of 162 g of 1-(4-chlorophenyl)-2,4-dimethyl-1-penten-3-one in 250 ml of NMP. The resulting mixture is heated at 60° C. for 30 min. The product obtained is left in the reaction mixture for the following stage.

Example 3

Preparation of
1-(4-chlorophenyl)-2-methyl-2-[2-(1-methylethyl)-2-oxiranyl]cyclopropane 151 g of trimethylsulphonium methyl sulphate in 200 ml of NMP are added to the solution obtained above at 25° C. The reaction is finished after 30 min. The compound obtained is left in the reaction mixture for the following stage.

Example 4

Preparation of
1-(4-chlorophenyl)-2-methyl-2-(2-methyl-1-hydroxy-1-(1,2,4-triazol-1ylmethyl)-1-propyl)cyclopropane
(compounds Nos. 3 and 4)

A solution of sodium triazole, obtained by mixing 60.5 g of 1,2,4-triazole and 70 g of 50% sodium hydroxide solution in 500 ml of NMP, is added to the solution obtained above. The reaction mixture is heated at 130° C. for 8 h. The mixture is then poured into 2 l of water and extracted with 2×750 ml of ether. The organic phase is washed with 2 l of water, then with 500 ml of saturated aqueous sodium chloride solution and dried over sodium sulphate. The crude product is purified by chromatography on silica with 60 heptane/37 ethylacetate/5 ethanol. 14.5 g of diastereoisomer A (M.p.=121° - compound 4) and 16.3 g of diastereoisomer B (M.p.=141° - compound 3) are obtained.

Example 5

Preparation of
2-(4-chlorophenyl)-4-(1,2,4-triazol-1-ylmethyl)-4-hydroxy-1-oxaspiro[2.5]octane (compound No. 7)

A mixture of 9 g of 2-(4-chlorobenzylidene)-1-(1,2,4-triazol-1-ylmethyl)cyclohexan-1-ol and 14.8 g of m-chloroperbenzoic acid in 50 ml of dichloromethane is stirred for 3 h at room temperature. 200 ml of water are then added and extracted with 3×100 ml of dichloromethane. The organic phase is washed with a potassium carbonate solution. The organic phase is dried over sodium sulphate and evaporated. The residue is crystallised from diisopropyl ether to produce 6 g of white solid (M.p.=150.5° C.)
Y=63%

| Compound No. | R¹ | R² | W | E | X | M.p. (°C.) |
|---|---|---|---|---|---|---|
| 1-(dia B) | iPr | Me | N | CH₂ | 2,4-diCl | 147 |
| 2-(dia A) | iPr | Me | N | CH₂ | 2,4-diCl | 145 |
| 3-(dia B) | iPr | Me | N | CH₂ | 4-Cl | 141 |
| 4-(dia A) | iPr | Me | N | CH₂ | 4-Cl | 121 |
| 5-(dia B) | iPr | Me | N | O | 4-Cl | 152 |
| 6-(dia A) | iPr | Me | N | O | 4-Cl | 175 |
| 7 | —(CH₂)₄— | | N | O | 4-Cl | 150 |
| 8 | —(CMe₂CH₂—CH₂)— | | N | O | 4-Cl | 143 |
| 9-(dia B) | tBu | Et | N | CH₂ | 4-Cl | 117 |
| 10-(dia A) | tBu | Et | N | CH₂ | 4-Cl | 100 |
| 11-(dia B) | iPr | Et | N | CH₂ | 4-Cl | 131 |
| 12-(dia A) | iPr | Et | N | CH₂ | 4-Cl | 109 |
| 13-(2 dia) | —(CMe₂CH—CH₂)— | | N | CH₂ | 4-Cl | 113 |
| 14-(dia A) | —(CHMeCH₂—CH₂—CH₂)— | | N | CH₂ | 4-Cl | 183 |
| 15-(dia A) | —(CH₂)₄— | | N | CH₂ | 4-Cl | 165 |
| 16-(dia B) | —(CH₂)₄— | | N | CH₂ | 4-Cl | 150 |
| 17-(dia A) | —(CH₂)₅— | | N | CH₂ | 4-Cl | 119 |
| 18-(dia B) | —(CH₂)₅— | | N | CH₂ | 4-Cl | 124 |
| 19-(dia A) | —(CHMeCH₂—CH₂)— | | N | CH₂ | 4-Cl | 128 |
| 20-(dia B) | —(CHMeCH₂—CH₂)— | | N | CH₂ | 4-Cl | 155 |
| 21-(dia C) | —(CHMeCH₂—CH₂)— | | N | CH₂ | 4-Cl | 157 |
| 22-(dia B) | —(CHMeCH₂—CH₂)— | | N | CH₂ | 4-Cl | 114 |
| 23-(dia C) | —(CHMeCH₂—CH₂)— | | N | CH₂ | 4-Cl | 161 |
| 24-(dia D) | —(CHMeCH₂—CH₂)— | | N | CH₂ | 4-Cl | 179 |
| 25 | —(CH₂)₃— | | N | CH₂ | 4-Cl | 123 |

Example 6

Preparation of 2-(4-chlorobenzylidene)-5-methyl-1-(methylthiomethyl)cyclopentanol 69 ml (0.011 mol) of 1.6M n-butyllithium are introduced, under argon, into a 500 ml round-bottomed flask equipped with a 100 ml pressure-equalising dropping funnel and a magnetic stirrer. The round-bottomed flask is cooled in an ice bath before successively running in 16.6 ml (0.11 mol) of tetramethylethylenediamine and then, after 15 min, 8.1 ml (0.11 mol) of dimethyl sulphide.

After stirring for 3 hours at room temperature, the round-bottomed flask is cooled to −70° C. before running in 20 g (0.09 mol) of 2-(4-chlorobenzylidene)-5-methylcyclopentanone dissolved in 100 ml of dry tetrahydrofuran.

After a half-hour at −70° C., 5 g of ammonium chloride and then 80 ml of ethyl ether are introduced into the round-bottomed flask. The solution is then hydrolysed with 200 ml of water saturated with ammonium chloride and extracted with 2 times 60 ml of ether. The organic phases are washed with 3 times 80 ml of water saturated with sodium chloride and then dried over magnesium sulphate.

After removal of the solvents, 25 g (crude yield: 98%) of 2-(4-chlorobenzylidene)-5-methyl-1-(methylthiomethyl)cyclopentanol are recovered in the form of a pale-yellow viscous oil having 2 diastereoisomers in the proportions 70/30.

Example 7

Preparation of [(1-(4-chlorophenyl)-5-methyl-4-hydroxyspiro[2.4]hept-4-yl)methyl]dimethylsulphonium iodide 11 g (0,168 g.at) of zinc powder in 60 ml of dry glyme are introduced, under nitrogen, into a 250 ml round-bottomed flask equipped with a reflux condenser, a pressure-equalising dropping funnel and a mechanical stirrer. The round-bottomed flask is then introduced into an ultrasound bath (Branson 2200 model) for 1 h 30 min before rapidly introducing 13.5 g (0.048 mol) of the compound prepared in Example 6, diluted in 10 ml of glyme. Then, under ultrasound, 13.7 ml (0.170 mol) of diiodomethane, diluted with 10 ml of glyme, are run in dropwise at 45° C. A significant exotherm of 10° to 15° C. is observed during the introduction of the diiodomethane. The mixture is maintained for 5 h, with ultrasound, at 55° C.

After having allowed the temperature to return to room temperature, 100 ml of ethyl acetate are added before hydrolysing with 150 ml of a solution of water saturated with ammonium chloride. The aqueous phase is extracted with 3 times 70 ml of ethyl acetate. The combined organic phases are washed, with 3 times 80 ml of water saturated with sodium chloride, dried over magnesium sulphate and concentrated.

35 g of a pale-yellow viscous oil are collected, which oil is triturated with a 50/50 mixture of ethyl ether/diisopropyl ether and gives a very hygroscopic beige precipitate. After drying at 40° C., 18 g (yield: 87%) of a mass in the form of a white foam melting at 78° C. are obtained.

Example 8

Preparation of 1-(4-chlorophenyl)-4-(1H-1,2,4-triazol-1-ylmethyl)-5-methyl-4-hydroxyspiro[2.4]heptane (compounds 19 and 21)

160 ml of dry dimethyl formamide and then 1.64 g (0.04 mol) of 60% sodium hydride in oil are introduced into a 500 ml round-bottomed flask equipped with a reflux condenser, a 100 ml dropping funnel and a mechanical stirrer. 7.64 g (0.084 mol) of sodium triazole, prepared and diluted in 40 ml of dimethylformamide, are added.

The mixture is then heated at 85° C. for 3 hours. After having allowed the temperature to return to room temperature, the mixture is hydrolysed and treated as in Example 4.

After removal of the solvents, 10.5 g of a brown viscous residue are obtained, which residue, by chromatography on a silica column (eluent: methylene chloride/methanol 98/2), gives 5.9 g of a mixture of the compounds 19 and 21 in the proportions 30/70 (overall yield: 41%).

Compound 21 is obtained by recrystallisation of the above mixture with the two-component mixture ethyl acetate/diisopropyl ether. Melting point: 157° C.

Compounds 2, 4, 10, 12, 16, 17, 22, 24 and 25 can also be obtained according to this process.

Example 9

In vivo test on *Botrytis cinerea* (grey mould) on excised tomato leaf (strains sensitive and resistant to benzimidazoles An aqueous suspension of the active material to be tested, having the following composition, is prepared, by fine milling:
  active material: 60 mg
  surface-active agent Tween 80 (oleate of polyoxyethylenated derivative of sorbitan) diluted to 10% in water: 0.3 ml
  made up to 60 ml with water to obtain a 1 g/l suspension/solution.

This aqueous suspension is then optionally diluted with water to obtain the desired concentration of active material.

Tomatoes cultivated under glass (variety Marmande), 30 days old, are treated by spraying with aqueous suspensions as defined above and at various concentrations of the test compound.

Seedlings, used as controls, are treated with an aqueous solution which does not contain the active material.

After 24 hours, the leaves are cut and put in a Petri dish (diameter 14 cm), the bottom of which was covered beforehand with a wet filter paper disc (10 leaflets per dish).

The inoculum is then introduced, using a syringe, by deposition of drops (3 per leaflet) of a suspension of spores of *Botrytis cinerea*, which are sensitive to benzimidazoles or resistant to benzimidazoles, which suspension is obtained from 15-day cultures subsequently suspended at a concentration of 150,000 units per cm$^3$.

Inspection is carried out 6 days after infection by comparison with an untreated control.

Under these conditions, at a dose of 1 g/l, a good (at least 75%) or total protection is observed with compounds 1, 3, 4, 5, 6, 7, 8, 10, 12, 13, 16, 17, 19, 22 and 23 against those strains of Botrytis which are sensitive to benzimidazoles.

Example 10

In vivo test on *Piricularia oryzae* responsible for piriculariosis in rice

An aqueous suspension of the active material to be tested, having the following composition, is prepared, by fine milling:
  active material: 60 mg
  surface-active agent Tween 80 (oleate of polyoxyethylenated derivative of sorbitan) diluted to 10% in water: 0.3 ml
  made up to 60 ml with water to obtain a 1 g/l suspension/solution.

This aqueous suspension is then optionally diluted with water to obtain the desired concentration of active material.

Rice, seeded in small pots in a 50/50 mixture of enriched peat and pozzolana, is treated at the 10 cm-high stage by spraying with the above aqueous suspension.

Seedlings, used as controls, are treated with an aqueous solution which does not contain the active material.

After 24 hours, an aqueous suspension of spores of Piriculariaoryzae, which spores are obtained from a 15-day culture and subsequently suspended at a concentration of 100,000 units per cm$^3$, is applied to the leaves.

The rice plants are incubated for 24 hours (25° C., 100% relative humidity) and are then put in an observation cell, under the same conditions, for 5 days.

Reading is carried out 6 days after infection.

Under these conditions, at a dose of 1 g/l, a good (at least 75%) or total protection is observed with compounds 2, 3, 4, 5, 6, 8, 10, 11, 12, 13, 14, 16, 17, 19, 21, 22, 23 and 24.

Example 11

In vivo test on *Erysiphe graminis* on barley (barley powdery mildew)

An aqueous suspension of the active material to be tested, having the following composition, is prepared, by fine milling:
  active material: 60 mg
  surface-active agent Tween 80 (oleate of polyoxyethylenated derivative of sorbitan) diluted to 10% in water: 0.3 ml
  made up to 60 ml with water to obtain a 1 g/l suspension/solution.

This aqueous suspension is then optionally diluted with water to obtain the desired concentration of active material.

Barley, in small pots, seeded on a 50/50 peat/pozzolana substrate, is treated at the 10 cm-high stage by spraying with the above aqueous suspension.

Seedlings, used as controls, are treated with an aqueous solution which does not contain the active material.

After 24 hours, the barley seedlings are dusted with spores of *Erysiphe graminis*, the dusting being carried out using diseased seedlings.

Reading is carried out 7 to 14 days after infection, in comparison with the control seedlings.

Under these conditions, at a dose of 1 g/l, a good (at least 75%) or total protection is observed with compounds 1, 2, 4, 5, 6, 8, 10, 12, 13, 16, 19, 20, 21, 22, 23 and 24.

Example 12

In vivo test on *Puccinia recondita* (wheat brown rust)

An aqueous suspension of the active material to be tested, having the following composition is prepared, by fine milling:
  active material: 60 mg
  surface-active agent Tween 80 (oleate of polyoxyethylenated derivative of sorbitan) diluted to 10 % in water: 0.3 ml
  made up to 60 ml with water to obtain a 1 g/l suspension/solution.

This aqueous suspension is then optionally diluted with water to obtain the desired concentration of active material.

Wheat, in small pots, seeded on a 50/50 peat/pozzolana substrate, is treated at the 10 cm-high stage by spraying with the above aqueous suspension.

Seedlings, used as controls, are treated with an aqueous solution which does not contain the active material.

After 24 hours, an aqueous suspension of spores (100,000 sp/cm$^3$) is sprayed on the wheat; this suspension was obtained from infected seedlings. The wheat is then placed for 24 hours in an incubation cell at approximately 20° C. and at 100% relative humidity, and then for 7 to 14 days at 60% relative humidity.

Monitoring of the condition of the seedlings is carried out between the 8th and 15th day after infection, by comparison with an untreated control.

Under these conditions, at a dose of 1 g/l, a good (at least 75%) or total protection is observed with the following compounds 1, 3, 4, 6, 7, 8, 9, 10, 11, 12, 13, 16, 22, 23 and 24.

These results clearly show the good fungicidal properties of the derivatives according to the invention against plant diseases due to fungi belonging to the most diverse families, such as the Phycomycetes, Basidiomycetes, Ascomycetes, Adelomycetes or Fungi Imperfecti, in particular the Botrytis species, *Piricularia oryzae*, powdery mildews (Erysiphe sp.), rusts (Puccinia sp.) and grape downy mildew.

In fact, the compounds according to the invention are rarely used alone in practice. These compounds are most often part of compositions. These compositions, which can be used as fungicidal agents, contain a compound according to the invention, as described earlier, as active material mixed with solid or liquid vehicles, which are acceptable in agriculture, and surface-active agents which are also acceptable in agriculture. In particular, the inert and conventional vehicles and the conventional surface-active agents can be used. These compositions also form part of the invention.

These compositions can also contain any kind of other ingredients such as, for example, protective colloids, adhesives, thickening agents, thixotropic agents, penetrating agents, stabilising agents, sequestering agents and the like. More generally, the compounds used in the invention can be combined with all the solid or liquid additives corresponding to the conventional formulating techniques.

Generally, the compositions according to the invention usually contain from approximately 0.05 to 95% (by weight) of a compound according to the invention (subsequently called active material), one or more solid or liquid vehicles and, optionally, one or more surface-active agents.

In the present account, the term "vehicle" denotes a natural or synthetic, organic or inorganic material with which the compound is combined to facilitate its application on the plant, on seeds or on the ground. This vehicle is thus generally inert and it must be acceptable in agriculture, especially on the treated plant. The vehicle can be solid (clays, natural or synthetic silicates, silica, resins, waxes, solid fertilisers and the like) or liquid (water, alcohols, especially butanol, and the like).

The surface-active agent can be an emulsifying, dispersing or wetting agent of ionic or nonionic type or a mixture of such surface-active agents. There may be mentioned, for example, salts of polyacrylic acids, salts of lignosulphonic acids, salts of phenolsulphonic or naphthalenesulphonic acids, polycondensates of ethylene oxide with fatty alcohols or with fatty acids or with fatty amines, substituted phenols, (especially alkylphenols or arylphenols), salts of esters of sulphosuccinic acids, taurine derivatives (especially alkyltaurates), phosphoric esters of polyoxyethylenated phenols or alcohols, esters of fatty acids and of polyols, and the derivatives of the above compounds containing sulphate, sulphonate and phosphate functional groups. The presence of at least one surface-active agent is generally indispensable when the compound and/or the inert vehicle is/are not soluble in water and the carrier agent for application is water.

The compositions for agricultural use according to the invention can thus contain the active materials according to the invention within very wide limits, ranging from 0.05% to 95% (by weight). Their surface-active agent content is advantageously of between 5% and 40% by weight.

These compositions according to the invention are themselves in fairly diverse, solid or liquid forms.

There may be mentioned, as forms of solid compositions, the powders for dusting (with a compound content which can range up to 100%) and the granules, especially those obtained by extrusion, by compacting, by impregnation of a granulated support, or by granulation from a powder (the compound content in these granules being between 0.5 and 80% for the latter cases), the tablets or effervescent tablets.

The compounds of formula (I) can also be used in the form of powders for dusting; it is also possible to use a composition comprising 50 g of active material and 950 g of talc; it is also possible to use a composition comprising 20 g of active material, 10 g of finely divided silica and 970 g of talc; these constituents are mixed and milled and the mixture is applied by dusting.

There may be mentioned, as forms of liquid compositions or those intended to constitute liquid compositions at the time of application, solutions, in particular water-soluble concentrates, emulsifiable concentrates, emulsions, suspension concentrates, aerosols, wettable powders (or powder to be sprayed), pastes or gels.

The emulsifiable or soluble concentrates most often comprise 10 to 80% of active material while emulsions or solutions ready for application contain 0.001 to 20% of active material.

In addition to the solvent, the emulsifiable concentrates can contain, when this is necessary, 2 to 20% of suitable additives such as stabilising agents, surface-active agents, penetrating agents, corrosion inhibitors, dyes or the abovementioned adhesives.

From these concentrates, it is possible to obtain, by dilution with water, emulsions of any desired concentration, which are particularly suitable for application to crops.

The compositions of some emulsifiable concentrates are given here as examples:

EC Example 1

| active material | 400 g/l |
| --- | --- |
| alkali metal dodecylbenzenesulphonate | 24 g/l |
| oxyethylenated nonylphenol, containing 10 molecules of ethylene oxide | 16 g/l |
| cyclohexanone | 200 g/l |
| aromatic solvent | qs 1 liter |

Another emulsifiable concentrate formula uses:

EC Example 2

| active material | 250 g |
| --- | --- |
| epoxidised vegetable oil | 25 g |
| mixture of alkylaryl sulphonate and ether of polyglycol and fatty alcohols | 100 g |
| dimethylformamide | 50 g |
| xylene | 575 g |

The suspension concentrates, also applicable by spraying, are prepared so as to obtain a stable fluid product which does not settle out and they generally contain from 10 to 75% of active material, from 0.5 to 15% of surface-active agents, from 0.1 to 10% of thixotropic agents and from 0 to 10% of suitable additives, such as antifoaming agents, corrosion inhibitors, stabilising agents, penetrating agents and adhesives and, as vehicle, water or an organic liquid in which the active material is insoluble or nearly insoluble: certain organic solid materials or inorganic salts can be dissolved in the vehicle to aid in preventing sedimentation or as antigels for water.

A suspension concentrate composition is given here as an example:

SC Example 1

| | |
|---|---|
| active material | 500 g |
| polyethoxylated tristyrylphenyl phosphate | 50 g |
| polyethoxylated alkylphenol | 50 g |
| sodium polycarboxylate | 20 g |
| ethylene glycol | 50 g |
| organopolysiloxane oil (antifoaming agent) | 1 g |
| polysaccharide | 1.5 g |
| water | 316.5 g |

Wettable powders (or powder to be sprayed) are generally prepared so that they contain 20 to 95% of active material, and they generally contain, in addition to the solid vehicle, from 0 to 30% of a wetting agent, from 3 to 20% of a dispersing agent and, when this is necessary, from 0.1 to 10% of one or more stabilising agents and/or other additives, such as penetrating agents, adhesives, or anticlumping agents, dyes, and the like.

To obtain powders to be sprayed or wettable powders, the active materials are intimately mixed, in suitable mixers, with the additional substances and the mixture is milled with mills or other suitable grinders. Powders to be sprayed are thereby obtained with advantageous wettability and suspensibility; they can be suspended in water at any desired concentration and these suspensions can be used very advantageously in particular for application to plant leaves.

Pastes can be produced in place of wettable powders. The conditions and modes of production and use of these pastes are similar to those of wettable powders or powders to be sprayed.

Various wettable powder (or powder to be sprayed) compositions are given here as examples:

WP Example 1

| | |
|---|---|
| active material | 50% |
| ethoxylated fatty alcohol (wetting agent) | 2.5% |
| ethoxylated phenylethylphenol (dispersing agent) | 5% |
| chalk (inert vehicle) | 42.5% |

WP Example 2

| | |
|---|---|
| active material | 10% |
| C13 branched-type synthetic oxo alcohol, ethoxylated with 8 to 10 molecules of ethylene oxide (wetting agent) | 0.75% |
| neutral calcium lignosulphonate (dispersing agent) | 12% |
| calcium carbonate (inert vehicle) | qs 100% |

WP Example 3

This wettable powder contains the same ingredients as in the above example, in the proportions below:

| | |
|---|---|
| active material | 75% |
| wetting agent | 1.50% |
| dispersing agent | 8% |
| calcium carbonate (inert vehicle) | qs 100% |

WP Example 4

| | |
|---|---|
| active material | 90% |
| ethoxylated fatty alcohol (wetting agent) | 4% |
| ethoxylated phenylethylphenol (dispersing agent) | 6% |

WP Example 5

| | |
|---|---|
| active material | 50% |
| mixture of anionic and nonionic surface-active agents (wetting agent) | 2.5% |
| sodium lignosulphonate (dispersing agent) | 5% |
| kaolin clay (inert vehicle) | 42.5% |

Aqueous dispersions and emulsions, for example the compositions obtained by diluting a wettable powder or an emulsifiable concentrate according to the invention with water, are contained within the general scope of the present invention. Emulsions can be of the water-in-oil or oil-in-water type and they can have a thick consistency, like that of a "mayonnaise".

The compounds according to the invention can be formulated in the form of water-dispersible granules, which are also contained within the scope of the invention.

These dispersible granules, with a bulk density generally of between approximately 0.3 and 0.6, have a particle size generally of between approximately 150 and 2000 and preferably between 300 and 1500 microns.

The active material content of these granules is generally between approximately 1% and 90%, and preferably between 25% and 90%.

The rest of the granule is essentially composed of a solid filler and, optionally, of surface-active adjuvants which confer water-dispersibility properties on the granule. These granules can be essentially of two distinct types according to whether the filler used is soluble or insoluble in water. When the filler is water-soluble, it can be inorganic or, preferably, organic. Excellent results were obtained with urea. In the case of an insoluble filler, the latter is preferably inorganic, such as, for example, kaolin or bentonite. It is then advantageously accompanied by surface-active agents (in a proportion of 2 to 20% by weight of the granule) of which more than half consists of, for example, at least one dispersing agent, essentially anionic, such as an alkali metal or alkaline-earth metal polynaphthalenesulphonate or an alkali metal or alkaline-earth metal lignosulphonate, the remainder consisting of nonionic or anionic wetting agents such as an alkali metal or alkaline-earth metal alkylnaphthalenesulphonate.

Moreover, although this is not indispensable, it is possible to add other adjuvants such as antifoaming agents.

The granule according to the invention can be prepared by mixing the necessary ingredients and then granulating according to several techniques known per se (granulator, fluid bed, sprayer, extrusion, and the like). The preparation generally finishes with a crushing followed by a sieving to the particle size chosen within the limits mentioned above. Granules obtained as above and then impregnated with a composition containing the active material can also be used.

They are preferably obtained by extrusion, by carrying out the preparation as indicated in the examples below.

DG Example 1

Dispersible granules

90% by weight of active material and 10% of urea in the form of pearls are mixed in a mixer. The mixture is then milled in a pin mill. A powder is obtained which is moistened with approximately 8% by weight of water. The moist powder is extruded in a perforated-roller extruder. A granular material is obtained which is dried, and then crushed and sieved, so as to respectively keep only the granules with a size of between 150 and 2000 microns.

DG Example 2

Dispersible granules

The following constituents are mixed in a mixer:

| | |
|---|---|
| active material | 75% |
| wetting agent (sodium alkylnaphthalene-sulphonate | 2% |
| dispersing agent (sodium polynaphthalene-sulphonate) | 8% |
| water-insoluble inert filler (kaolin) | 15% |

This mixture is granulated on a fluid bed in the presence of water and then dried, crushed and sieved so as to obtain granules with a size of between 0.15 and 0.80 mm.

These granules can be used alone or in solution or dispersion in water so as to obtain the required dose. They can also be used to prepare combinations with other active materials, especially fungicides, the latter being in the form of wettable powders or granules or aqueous suspensions.

As regards the compositions which are suitable for storage and transportation, they most advantageously contain from 0.5 to 95% (by weight) of active substance.

Another subject of the invention is the use of the compounds according to the invention for combating fungal diseases in plants by preventative or curative treatment of the latter or of their growth site.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. A compound having the formula

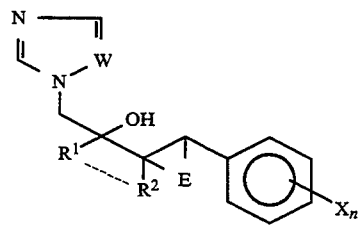

(VII)

or an agriculturally acceptable salt thereof, wherein:

E is an oxygen atom or a $CH_2$ radical;

$R^1$ and $R^2$, taken together, are a $-(CH_2)_3-$, $-(CH_2)_4-$ or $-(CH_2)_5-$ radical, said radical forming, together with the carbon atoms to which it is attached, a ring having 5, 6 or 7 ring carbon atoms, wherein each hydrogen can optionally be replaced by a substituent selected from the group consisting of a halogen atom and a straight or branched-chain alkyl radical having up to 4 carbon atoms, optionally substituted by one or more halogen atoms;

W is a nitrogen atom;

X is a halogen atom; a straight or branched-alkyl radical having up to 4 carbon atoms, optionally substituted by one or more halogen atoms; an alkylamino radical, the alkyl portion having from 1 to 4 carbon atoms, optionally substituted by one or more halogen atoms; an alkoxy radical having 1 to 4 carbon atoms, optionally substituted by one or more halogen atoms; a phenoxy or benzyloxy radical which is optionally substituted by one or more halogen atoms; nitro; or cyano; and n is an integer equal to 1, 2, 3, 4 or 5, provided that when n is equal to or greater than 2, then the groups represented by X can be the same or different.

2. A compound according to claim 1, wherein the halogen atom represented by X is a fluorine, chlorine or bromine atom.

3. A compound according to claim 1, wherein the halogen atom represented by $R^2$ is a chlorine or fluorine atom.

4. A compound according to claim 1, wherein E is an oxygen atom.

5. A compound according to claim 1, wherein E is a $CH_2$ radical.

6. A compound according to claim 4, wherein X is a halogen atom.

7. A compound according to claim 5, wherein X is a halogen atom.

8. A compound according to claim 6, wherein X is a chlorine atom.

9. A compound according to claim 7, wherein X is a chlorine atom.

10. A compound according to claim 1, wherein $R^1$ and $R^2$, taken together, are a $-(CH_2)_3-$ or $-(CH_2)_4-$ radical, said radical forming, together with the carbon atoms to which it is attached, a ring having 5 or 6 ring carbon atoms, wherein each hydrogen can optionally be replaced by a substituent selected from the group consisting of a halogen atom and a straight or branched-chain alkyl radical having up to 4 carbon atoms, optionally substituted by one or more halogen atoms.

11. A compound according to claim 10, wherein each of up to 2 hydrogens can optionally be replaced by a methyl radical.

12. A compound according to claim 11, wherein $R^1$ and $R^2$, taken together, are —$(CH_2)_4$—, —$(CMe_2CH_2-CH_2)$—, —$(CHMeCH_2-CH_2-CH_2)$—, —$(CHMeCH_2-CH_2)$— or —$(CH_2)_3$—.

13. A compound according to claim 6, wherein n is 1 or 2.

14. A compound according to claim 7, wherein n is 1 or 2.

15. The compound according to claim 1, wherein:

$R^1$ and $R^2$ taken together are —$(CH_2)_4$—, W is N, E is O and X is 4-chloro;

$R^1$ and $R^2$ taken together are —$(CMe_2CH_2-CH_2)$—, W is N, E is O and X is 4-chloro;

$R^1$ and $R^2$ taken together are —$(CMe_2CH_2-CH_2)$—, W is N, E is $CH_2$ and X is 4-chloro;

$R^1$ and $R^2$ taken together are —$(CHMeCH_2-CH_2-CH_2)$—, W is N, E is $CH_2$ and X is 4-chloro;

$R^1$ and $R^2$ taken together are —$(CH_2)_4$—, W is N, E is $CH_2$ and X is 4-chloro;

$R^1$ and $R^2$ taken together are —$(CH_2)_5$—, W is N, E is $CH_2$ and X is 4-chloro;

$R^1$ and $R^2$ taken together are —$(CHMeCH_2-CH_2)$—, W is N, E is $CH_2$ and X is 4-chloro; or $R^1$ and $R^2$ taken together are —$(CH_2)_3$—, W is N, E is $CH_2$ and X is 4-chloro.

16. A fungicidal composition comprising a fungicidally effective amount of a compound having formula (VII) as claimed in claim 1 or an agriculturally acceptable salt thereof, and at least one member selected from the group consisting of agriculturally acceptable vehicles and agriculturally acceptable surface-active agents.

17. The fungicidal composition according to claim 16, wherein said fungicidally effective amount is from about 0.05 to about 95% by weight of the total composition.

18. A method for the treatment of crops affected by or capable of being affected by fungal disease, said method comprising preventatively or curatively applying to said crops a fungicidally effective amount of a compound of formula (VII) as claimed in claim 1 or an agriculturally acceptable salt thereof.

19. A method for the treatment of crops affected by or capable of being affected by fungal disease, said method comprising preventatively or curatively applying to said crops a fungicidally effective amount of a composition as claimed in claim 16.

20. The method according to claim 18, wherein said fungicidally effective amount is applied at a rate of between about 0.002 and about 5 kg/ha.

21. The method according to claim 20, wherein said fungicidally effective amount is applied at a rate of between about 0.005 and about 1 kg/ha.

22. The method according to claim 18, wherein said fungicidally effective amount is applied to the leaves of said crops.

23. The compound according to claim 1, which is 1-(4-chlorophenyl)-4-(1H-1,2,4-triazol-1-ylmethyl)-5-methyl-4-hydroxyspiro[2.4]heptane.

* * * * *